(12) United States Patent
Zhang et al.

(10) Patent No.: US 12,222,115 B2
(45) Date of Patent: Feb. 11, 2025

(54) AIR PURIFICATION DEVICE

(71) Applicant: Carrier Corporation, Palm Beach Gardens, FL (US)

(72) Inventors: Shuguang Zhang, Shanghai (CN); Yuhui Kuang, Shanghai (CN); Hui Zhai, Shanghai (CN); Guangyu Shen, Shanghai (CN); Hongsheng Liu, Shanghai (CN); Michael J. Birnkrant, Wethersfield, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 552 days.

(21) Appl. No.: 17/591,913

(22) Filed: Feb. 3, 2022

(65) Prior Publication Data
US 2022/0252280 A1    Aug. 11, 2022

(30) Foreign Application Priority Data
Feb. 7, 2021  (CN) .......................... 202110176088.2

(51) Int. Cl.
*F24F 1/0353*  (2019.01)
*F24F 3/16*  (2021.01)
*F24F 7/08*  (2006.01)
*F24F 11/89*  (2018.01)

(52) U.S. Cl.
CPC ............ *F24F 1/0353* (2019.02); *F24F 3/16* (2013.01); *F24F 7/08* (2013.01); *F24F 11/89* (2018.01)

(58) Field of Classification Search
None
See application file for complete search history.

(56) References Cited

U.S. PATENT DOCUMENTS

| | | |
|---|---|---|
| 5,401,299 A | 3/1995 | Kroeger et al. |
| 5,656,063 A | 8/1997 | Hsu |
| 5,759,487 A | 6/1998 | Jung |
| 7,431,752 B2 | 10/2008 | Liang |
| 9,308,492 B2 | 4/2016 | Obee et al. |
| 2003/0108460 A1 | 6/2003 | Andreev et al. |

(Continued)

FOREIGN PATENT DOCUMENTS

| | | |
|---|---|---|
| CN | 103836774 A | 6/2014 |
| CN | 204578879 U * | 8/2015 |

(Continued)

OTHER PUBLICATIONS

Machine translation of CN 204578879 U (Year: 2015).*

(Continued)

*Primary Examiner* — Natasha E Young
(74) *Attorney, Agent, or Firm* — CANTOR COLBURN LLP

(57) ABSTRACT

An air purification includes a body portion, having a first installation space, a second installation space and a third installation space; a positive/negative ion module, removably mounted in the first installation space and controlled to generate positive ions and/or negative ions; a plasma module, removably mounted in the second installation space and controlled to generate plasmas; and a power supply module, removably mounted in the third installation space and configured to supply power for the positive/negative ion module and the plasma module.

11 Claims, 1 Drawing Sheet

(56) References Cited

U.S. PATENT DOCUMENTS

2016/0156160 A1    6/2016  Waddell et al.
2017/0341088 A1*  11/2017  Chen ..................... B03C 3/41

FOREIGN PATENT DOCUMENTS

| | | |
|---|---|---|
| CN | 208332526 U | 1/2019 |
| ES | 1225789 U | 3/2019 |
| WO | 2020248566 A1 | 12/2020 |

OTHER PUBLICATIONS

Foreign Patent CN 205960959 U (Year: 2017).*
English Abstract of CN 205960959 U (Year: 2017).*
European Search Report for application EP 22155497.5, dated Jun. 21, 2022, 102 pages.
Global Plasma Solutions, "The Value of Auto-Cleaning for Needlepoint Bipolar Ionization Systems", White Paper, Oct. 1, 2019, 4 pages.
Hyun, Junho et al., "Applicaiton of corona discharge-generated air ions for filtration of aersolized virus and inactivation of filtered virus", Journal of Aerosol Science, 2017, 10 pages.
Liu, Linmao, et al., "The effect of wire heating and configuration on ozone emission in a negative ion generator", Journal of Electrostatics, 2000, 11 pages.
Meschke, S., et al., "The effect of surface charge, negative and bipolar ionization on the deposition of airborne bacteria", Journal of Applied Microbiology, 7 pages.
Murata Iie, "Murata Ionisiomo Solution 2020 (Ionizer and Ozonizer)", XP055927696, Nov. 5, 2020, 32 pages.
Nunyon, Sunday, S., et al., "Experimental evaluation of positive and negative air ions disinfection efficacy under different ventilation duct conditions", Building and Environment, 2019, 7 pages.
Park, Jin-Soo, et al., "The bactericidal effect of an ionizer under low concentration of ozone", BMC Microbiology, 2016, 3 pages.
Plank, Toomas, et al., "Ozone generation efficiency as a function of electric field strength in air", Journal of Physics, Applied Physics, 2014, 6 pages.

* cited by examiner

AIR PURIFICATION DEVICE

FOREIGN PRIORITY

This application claims priority to Chinese Patent Application No. 202110176088.2, filed Feb. 7, 2021, and all the benefits accruing therefrom under 35 U.S.C. § 119, the contents of which in its entirety are herein incorporated by reference.

TECHNICAL FIELD

The present disclosure relates to the field of air conditioning. More specifically, the present invention relates to an air purification device.

BACKGROUND

Air purification equipment belongs to an emerging and rapidly developing field in recent years, and it plays a role in improving air quality. The rapid development of air purification equipment has benefited from human beings' increasing attention to the impact of the living environment on healthy. For example, particulates such as PM2.5, formaldehyde or other volatile organic compounds (VOCs) are harmful to health and are extremely common in the current living environment. Therefore, it is desirable to provide an air purification equipment to eliminate these hazards.

Currently, many types of air purification technologies are used in the market. For example, there are various purification filter elements focusing on physical adsorption technology or chemical catalytic technology. For another example, there are negative ion purifiers, positive/negative ion purifiers or plasma purifiers etc. that use air ionization technology. These purification technologies have their own advantages and disadvantages. For example, various purification filter elements have outstanding purification performance, but their service life is relatively short and they need to be replaced more frequently; plasma purifiers have better ionization purification performance, but they generate by-products correspondingly such as ozone; while the negative ion purifiers or positive/negative ion purifiers do not generate by-products, but they have relatively weaker ionization purification performance. Thus, considering the prior art of air purification technology, there is a need for making appropriate choices based on the specific needs of the application scenario.

SUMMARY

The present disclosure aims to provide an air purification device, so as to at least partially solve or mitigate problems existing in the prior art.

In order to achieve at least one objective of the present application, according to one aspect of the present application, an air purification device is provided, which comprises: a body portion, having a first installation space, a second installation space and a third installation space; a positive/negative ion module, removably mounted in the first installation space and controlled to generate positive ions and/or negative ions; a plasma module, removably mounted in the second installation space and controlled to generate plasmas; and a power supply module, removably mounted in the third installation space and configured to supply power for the positive/negative ion module and the plasma module.

Optionally, the air purification device comprises multiple air purification settings. Each of the air purification settings corresponds to different output voltages of the power supply module, different levels of positive/negative ions generated by the positive/negative ion module and different levels of plasmas generated by the plasma module.

Optionally, the power supply module has a first low output voltage and a first high output voltage for the positive/negative ion module, the positive/negative ion module generates low level of positive/negative ions and high level of positive/negative ions, respectively; and the power supply module has a second low output voltage and a second high output voltage for the plasma module, the plasma module generates low level of plasmas and high level of plasmas, respectively.

Optionally, the air purification settings comprise: a first-stage air purification setting, wherein the power supply module is controlled to supply power to the positive/negative ion module, so that the positive/negative ion module generates positive/negative ions; and a second-stage air purification setting, wherein the power supply module is controlled to supply power to the positive/negative ion module and the plasma module, respectively, so that the positive/negative ion module generates positive/negative ions and the plasma module generates plasmas.

Optionally, the first-stage air purification setting comprises: a first low setting, wherein the power supply module is controlled to supply the positive/negative ion module with the first low output voltage, so that the positive/negative ion module generates low level of positive/negative ions; a first high setting, wherein the power supply module is controlled to supply the positive/negative ion module with the first high output voltage, so that the positive/negative ion module generates high level of positive/negative ions; and/or the second-stage air purification setting comprises: a second low setting, wherein the power supply module is controlled to supply the positive/negative ion module with the first low output voltage, so that the positive/negative ion module generates low level of positive/negative ions; and the power supply module is controlled to supply the plasma module with the second low output voltage, so that the plasma module generates low level of plasmas; a second middle setting, wherein the power supply module is controlled to supply the positive/negative ion module with the first high output voltage, so that the positive/negative ion module generates high level of positive/negative ions; and the power supply module is controlled to supply the plasma module with the second low output voltage, so that the plasma module generates low level of plasmas; a second high setting, wherein the power supply module is controlled to supply the positive/negative ion module with the first high output voltage, so that the positive/negative ion module generates high level of positive/negative ions; and the power supply module is controlled to supply the plasma module with the second high output voltage, so that the plasma module generates high level of plasmas.

Optionally, the air purification device further comprises a group of sensors for sensing, in the space of air to be conditioned, one or more parameters of: the content of volatile organic compounds, PM2.5, PM10, ozone level, room occupancy level, the number of human, human body temperature, positive/negative ion level and plasma level; wherein, a controller controls the output voltage of the power supply module supplied to the positive/negative ion module and/or the plasma module based on the one or more parameters sensed by the group of sensors.

Optionally, the air purification device further comprises a purification mode and a disinfect mode. Wherein, in the purification mode, the positive/negative ion module is controlled to generate only negative ions, or the positive/negative ion module is controlled to generate more negative ions than positive ions; or in the disinfect mode, the number of the negative ions which the positive/negative ion module is controlled to generate approaches the number of the positive ions which the positive/negative ion module is controlled to generate, or the plasma module is controlled to generate plasmas.

Optionally, the air purification device further comprises a controller configured to control the output voltage of the power supply module supplied to the positive/negative ion module and/or the plasma module, and the on/off state of the power supply module.

Optionally, the controller is configured as an internal controller integrated in the body portion; and/or the controller is configured as an external controller separated from the body portion.

Optionally, the external controller is mounted in the space of air to be conditioned and is integrated with temperature/humidity control module.

Optionally, the body portion of the air purification device is arranged at an air outlet or an air inlet of the space of air to be conditioned.

The air purification device according to the present application, by providing installation space for the positive/negative ion module and the plasma module in the body portion, enables these components to have better applicability, cost-effectiveness, and convenience for maintenance. In addition, since the arranged positive/negative ion module and the plasma module have a close output voltage application range, it is possible for the two modules to share power supply module. Compared to two conventional ionization purification devices, this can also save part of the hardware cost. Moreover, it is possible to manually or automatically control the output voltage of the power supply module supplied to the positive/negative ion module and/or the plasma module based on the specific needs of the application scenario, and thus to open/close or adjust the operating state of the two modules, whereby adaptive control can be achieved based on the requirements of air conditioning, a balance between the air purification performance and the reduction of by-products such as ozone can be reached, thereby maximizing revenue and reducing disadvantages.

DETAILED DESCRIPTION

Hereinafter, the present application will be described in detail with reference to exemplary embodiments in the accompanying drawings. However, it should be understood that this application can be implemented in many different forms, and should not be construed as being limited to the embodiments set forth herein. These embodiments are provided here for the purpose of making the disclosure of this application more complete and detailed, and fully conveying the concept of this application to those skilled in the art.

Figure 1:
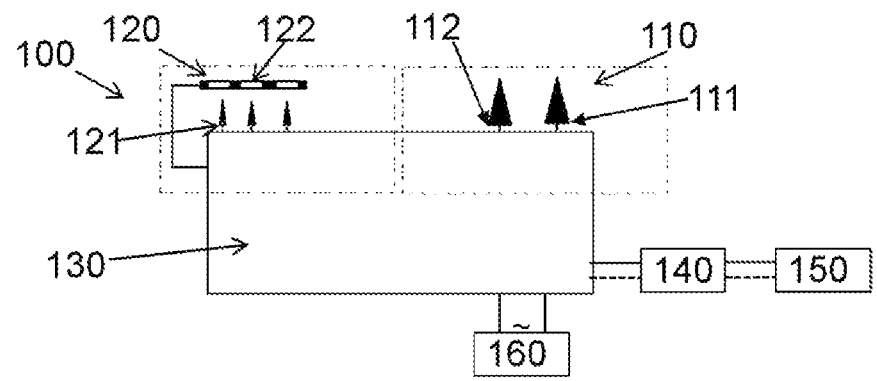
FIG. 1 is a system schematic diagram of an embodiment of an air purification device of the present application.

Referring to FIG. 1, it illustrates one embodiment of an air purification device according to the present application. The air purification device 100 comprises a body portion with a first installation space, a second installation space, and a third installation space for mounting the positive/negative ion module 110, the plasma module 120, and the power supply module 130, respectively. Wherein, the positive/negative ion module 110 is controlled to generate positive ions and/or negative ions, the plasma module 120 is controlled to generate plasmas, and the power supply module 130 is configured to supply power for the positive/negative ion module 110 and the plasma module 120. The air purification device 100 further optionally comprises a controller 140 for controlling the output voltage of the power supply module 130 supplied to the positive/negative ion module 110 and/or the plasma module 120 and the on/off state of the power supply module 130, thereby to achieve the control of the level of the ions output by the positive/negative ion module 110 and the level of the plasmas output by the plasma module 120.

Under such an arrangement, the air purification device 100, by providing installation space for the positive/negative ion module 110 and the plasma module 120 in the body portion, enables these components to have better applicability, cost-effectiveness, and convenience for maintenance. In addition, since the arranged positive/negative ion module 110 and the plasma module 120 have a close output voltage application range, it is possible for the two modules to share the power supply module 130. Compared to two conventional ionization purification devices, this can also save part of the hardware cost. Moreover, in some embodiments which comprise the internal controller 140, under the coordinated control of the controller, it is possible to control the output voltage of the power supply module 130 supplied to the positive/negative ion module 110 and/or the plasma module 120 based on the specific needs of the application scenario, and thus to open/close or adjust the operating state of the two modules, whereby adaptive control can be achieved based on the requirements of air conditioning, a balance between the air purification performance and the reduction of by-products such as ozone can be reached, thereby maximizing revenue and reducing disadvantages.

In addition, with regard to the foregoing embodiments, it should be mentioned that the applied positive/negative ion module 110 and the plasma module 120 can adopt the existing mature positive/negative ion generator and plasma generator.

For example, the positive/negative ion generator can generate a high voltage between the positive generating terminal 111 and the negative generating terminal 112 with a small power, thereby ionizing the air to generate positive/negative ions. The positive and negative ions release huge energy at the moment when they carry out positive and negative charges in the air, which leads to changes in the structure of the surrounding bacteria and energy transfer, and in turn leads to the death of bacteria, and realizes the effect of sterilization. It can also effectively decompose TVOC and other gaseous organic volatiles such as formaldehyde/benzene series/ammonia etc., thereby eliminating peculiar smell. In addition, the floating dust in the air will condense after encountering the polar ions, which will increase the mass of the particles and accelerate the sedimentation thereof. The charged particles will encounter the ground, surface and other fields where the potential is zero during the air movement, and then will be attached to the ground electrode, so that the floating dust will be converted into dustfall and the inhalable particles in the air will be reduced.

Wherein, the state with more negative ions is more helpful for dust removal, odor removal or even human health (for example, helpful for relieve asthma), and the state with a balance between positive and negative ions is more helpful for sterilization. Therefore, the controller can be configured accordingly so that in a purification mode, the controller controls the positive/negative ion module 110 to generate only negative ions, or the positive/negative ion module 110 generates more negative ions than positive ions; in a disinfect mode, the controller controls the number of the negative ions generated by the positive/negative ion module 110 to approach the number of the positive ions generated. Also, in the disinfect mode, the plasma module can be controlled to generate plasmas.

Again, for example, a plasma generator may generate plasmas by producing a strong electrical field between electrode generating terminal 121 and ground terminal 122, thereby achieving outstanding bactericidal performance, during which by-products as ozone may also be generated.

A further variant of the air purification device will be introduced in the following by way of exemplary illustration, for further improvement in its system efficiency, reliability, or for improvement in other aspects.

For example, in order to better coordinate the operating state of the positive/negative ion module and the plasma module under different application scenarios, multiple air purification settings are also provided through controllers. Wherein each of the air purification settings corresponds to different output voltages of the power supply module 130, such that different levels of positive/negative ions are generated by the positive/negative ion module 110 and different levels of plasmas are generated by the plasma module 120. At this time, the purification capabilities of the positive/negative ion module 110 and the plasma module 120 can be adjusted through the controller's control of the output voltage of the power supply module 130, so as to better balance the purification performance and the generation of by-products.

More specifically, the power supply module 130 has a first low output voltage and a first high output voltage for the positive/negative ion module 110, such that the positive/negative ion module 110 generates low level of positive/negative ions and high level of positive/negative ions, respectively; the power supply module 130 has a second low output voltage and a second high output voltage for the plasma module 120, such that the plasma module 120 generates low level of plasmas and high level of plasmas, respectively. At this time, the setting of the power supply module 130 ensures that these air ionization modules can be operated under at least two levels, which provides a hardware basis for the regulation of purification capabilities.

As an implementation of a type of air purification setting, the air purification setting may comprise: a first-stage air purification setting and a second-stage air purification setting. Wherein, the first-level air purification setting corresponds to a relatively low air purification requirement. At this time, the controller controls the power supply module 130 to supply power to the positive/negative ion module 110, such that the positive/negative ion module 110 generates positive/negative ions. On the one hand, the positive/negative ions bring a certain degree of air purification performance, and on the other hand, there are no by-products. The second-level air purification setting corresponds to a relatively high air purification requirement. At this time, the positive/negative ions generated by the positive/negative ion module 110 are usually not sufficient to meet the air purification requirements of the application scenario. Therefore, the controller controls the power supply module 130 to supply power to the positive/negative ion module 110 and the plasma module 120, respectively, such that the positive/negative ion module 110 generates positive/negative ions, and the plasma module 120 generates plasmas. Wherein, the plasmas generated by the plasma module 120 have a very strong air purification performance, but corresponding by-products such as ozone will be generated as well. Therefore, the method of turning on the plasma module 120 alone is not adopted. Rather, the method of turning on both of the two modules at the same time is adopted. It is intended to reduce a part of the workload of the plasma module 120 through the work of the positive/negative ion module 110, and accordingly reduce the by-products such as ozone generated by the plasma module 120.

More specifically, the aforementioned air purification setting can be further subdivided. As an embodiment of one type of subdivided setting, the first-stage air purification setting comprises a first low setting and a first high setting. Wherein, in the first low setting, the controller controls the power supply module 130 to supply the positive/negative ion module 110 with the first low output voltage, such that the positive/negative ion module 110 generates low level of positive/negative ions. In the first high setting, the controller controls the power supply module 130 to supply the positive/negative ion module 110 with a first high output voltage, such that the positive/negative ion module 110 generates high level of positive/negative ions. Although the positive/negative ion module will not generate by-products at any power, this type of subdivided settings can allow for providing air purification performance on demand, thereby improving efficiency and reducing unnecessary energy consumption.

The second-stage air purification setting also comprises a second low setting, a second middle setting, and a second high setting. Wherein, in the second low setting, the controller controls the power supply module 130 to supply the positive/negative ion module 110 with the first low output voltage, such that the positive/negative ion module 110 generates low level of positive/negative ions; and the controller controls the power supply module 130 to supply the plasma modules 120 with the second low output voltage, such that the plasma module 120 generates low level of plasmas. In the second middle setting, the controller controls the power supply module 130 to supply the positive/negative ion module 110 with the first high output voltage, such that the positive/negative ion module 110 generates high level of positive/negative ions; and the controller controls the power supply module 130 to supply the plasma module 120 with the second low output voltage, such that the plasma module 120 generates low level of plasmas. In the second high setting, the controller controls the power supply module 130 to supply the positive/negative ion module 110 with the first high output voltage, such that the positive/negative ion module 110 generates high level of positive/negative ions; and the controller controls the power supply module 130 to supply the plasma module 120 with the second high output voltage, such that the plasma module 120 generates high level of plasmas. This subdivision of the air purification setting shows the following tendency, that is, under the premise of meeting the same air purification capability, the use of the plasma module 120 is minimized or the use intensity of the plasma module 120 is reduced. At this time, the by-products caused by plasma purification will be reduced accordingly.

With respect to the embodiments of the air purification settings described above, it should be understood that, the aforementioned air purification settings can not only be automatically switched by the controller as discussed above, but also be switched manually. When the switching operation is carried out, if the corresponding determination condition is needed, it is also possible to arrange a group of sensors 150 for the air purification device, in order to sense, in the space of the air to be conditioned, one or more parameters of: the content of volatile organic compounds, PM2.5, PM10, ozone level, room occupancy level, the number of human, human body temperature, positive/negative ion level and plasma level. At this time, the controller may control the output voltage of the power supply module 130 supplied to the positive/negative ion module 110 and/or the plasma module 120 based on the one or more parameters sensed by the group of sensors 150, so as to carry out the automatic switching of the aforementioned air purification settings and to improve the adaptive adjustment capability of the device.

Figure 2:
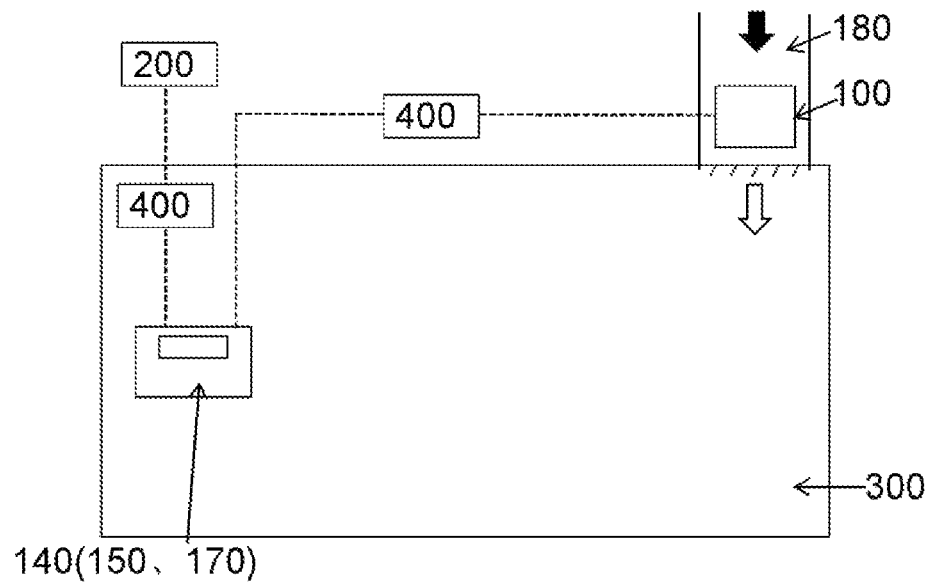
FIG. 2 is a system schematic diagram of another embodiment of an air purification device of the present application.

Again, referring to FIG. 2, it illustrates another embodiment of an air purification device according to the present application. Compared with the embodiment described with FIG. 1, the difference lies in that the air purification device 100 has an external controller 140, and the air purification device 100 can communicate with the external controller 140 and transmit sensed signals or control commands via a communication module 400, thereby facilitating manual operation by users when needed and improving convenience. In addition, the air purification device also has the technical effect corresponding to the air purification device mentioned in any of the foregoing embodiments or combinations thereof, which will not be repeated here.

Specifically, the external controller 140 of the air purification device 100 may be mounted in the space of air to be conditioned in the form of a control panel. On the one hand, the external controller 140 can be integrated with the group of sensors 150, in order to sense or collect the parameters of the space in close range and to improve the accuracy of sensing; on the other hand, the external controller 140 may also be integrated with a temperature/humidity control module 170, in order to achieve air temperature/humidity conditioning of the space.

Moreover, the body portion of the air purification device 100 may be arranged at the air outlet 180 of the space of the air to be conditioned, so that the air of which the temperature/humidity have already been conditioned could be conditioned further by the air purification device 100 before entering into the room, thereby improving the overall quality of the air conditioned. Optionally, the body portion of the air purification device 100 can also be arranged at the air inlet of the space of the air to be conditioned, to achieve a similar effect.

In the foregoing embodiment, it should be understood that, the air purification device 100 may be configured with corresponding hardware to realize the temperature/humidity conditioning function; also, the air purification device 100 may realize the temperature/humidity conditioning function by being integrated with the air conditioning system 200 or communicating via the communication module 400. Because the structural space of the air conditioning system 200 is limited, it is difficult to carry a large air purification filter element; and once the air conditioning equipment is installed, it is usually in a fixed state, so the replacement of the filter element in the air conditioning equipment is complicated. Such a modular air purification device 100 using ionization technology has low maintenance frequency and low space occupation, and has excellent compatibility with the air conditioning system 200.

Wherein, those skilled in the art should know that the air conditioning system proposed in this application does not narrowly refer to the air conditioners equipped with outdoor cooling/heating units and indoor heat exchange units used in buildings in the industry. Instead, it should be understood as a type of thermal system that has the function of air conditioning, which is driven by various power sources (for example, electric power) to exchange heat with the air at the position to be adjusted through the phase change of the refrigerant in the system. For example, when the air conditioning system is used for Heating Ventilating and Air Conditioning in buildings, it may be a cooling system with single cooling function, or it may be a heat pump system with both cooling and heating functions. For another example, when the air conditioning system is used in the cold chain field, it may be a transportation refrigeration system or a refrigeration/freezing system. However, no matter what kind of air conditioning system it is, the air conditioning system should have an air purification device so as to be suitable for the concept of this application.

The above example mainly describes the air purification device of the present invention. Although only some of the embodiments of the present invention have been described, those of ordinary skill in the art should understand that the present invention can be implemented in many other forms without departing from the spirit and scope thereof. Therefore, the examples and implementations shown are regarded as illustrative rather than restrictive, and the present invention may cover various modifications and replacements without departing from the spirit and scope of the present invention as defined by the appended claims.

What is claimed is:

1. An air purification device, characterized by, comprising:
    a body portion, having a first installation space, a second installation space and a third installation space;
    a positive/negative ion module removably mounted in the first installation space and controlled to generate positive ions and/or negative ions;
    a plasma module removably mounted in the second installation space and controlled to generate plasmas; and
    a power supply module removably mounted in the third installation space and configured to supply power for the positive/negative ion module and the plasma module.

2. The air purification device according to claim 1, wherein,
    the air purification device comprises multiple air purification settings, each of the air purification settings corresponds to different output voltages of the power supply module, different levels of positive/negative ions generated by the positive/negative ion module and different levels of plasmas generated by the plasma module.

3. The air purification device according to claim 2, wherein,
    the power supply module has a first low output voltage and a first high output voltage for the positive/negative ion module, such that the positive/negative ion module generates low level of positive/negative ions and high level of positive/negative ions, respectively; and
    the power supply module has a second low output voltage and a second high output voltage for the plasma module, the plasma module generates low level of plasmas and high level of plasmas, respectively.

4. The air purification device according to claim 3, wherein, the air purification settings comprise:
    a first-stage air purification setting, wherein the power supply module is controlled to supply power to the positive/negative ion module, so that the positive/negative ion module generates positive/negative ions; and a second-stage air purification setting, wherein the power supply module is controlled to supply power to the positive/negative ion module and the plasma module, respectively, so that the positive/negative ion module generates positive/negative ions and the plasma module generates plasmas.

5. The air purification device according to claim 4, wherein, the first-stage air purification setting comprises:

a first low setting, wherein the power supply module is controlled to supply the positive/negative ion module with the first low output voltage, so that the positive/negative ion module generates low level of positive/negative ions;

a first high setting, wherein the power supply module is controlled to supply the positive/negative ion module with the first high output voltage, so that the positive/negative ion module generates high level of positive/negative ions; and/or the second-stage air purification setting comprises:

a second low setting, wherein the power supply module is controlled to supply the positive/negative ion module with the first low output voltage, so that the positive/negative ion module generates low level of positive/negative ions; and the power supply module is controlled to supply the plasma module with the second low output voltage, so that the plasma module generates low level of plasmas;

a second middle setting, wherein the power supply module is controlled to supply the positive/negative ion module with the first high output voltage, so that the positive/negative ion module generates high level of positive/negative ions; and the power supply module is controlled to supply the plasma module with the second low output voltage, so that the plasma module generates low level of plasmas;

a second high setting, wherein the power supply module is controlled to supply the positive/negative ion module with the first high output voltage, so that the positive/negative ion module generates high level of positive/negative ions; and the power supply module is controlled to supply the plasma module with the second high output voltage, so that the plasma module generates high level of plasmas.

6. The air purification device according to claim 1, wherein, further comprising a group of sensors for sensing, in the space of air to be conditioned, one or more parameters of: the content of volatile organic compounds, PM2.5, PM10, ozone level, room occupancy level, the number of human, human body temperature, positive/negative ion level and plasma level; wherein, a controller controls the output voltage of the power supply module supplied to the positive/negative ion module and/or the plasma module based on the one or more parameters sensed by the group of sensors.

7. The air purification device according to claim 1, further comprising a purification mode and a disinfect mode, wherein in the purification mode, the positive/negative ion module is controlled to generate only negative ions, or the positive/negative ion module is controlled to generate more negative ions than positive ions; or in the disinfect mode, the number of the negative ions which the positive/negative ion module is controlled to generate approaches the number of the positive ions which the positive/negative ion module is controlled to generate, or the plasma module is controlled to generate plasmas.

8. The air purification device according to claim 1, wherein, further comprising a controller configured to control the output voltage of the power supply module supplied to the positive/negative ion module and/or the plasma module, and the on/off state of the power supply module.

9. The air purification device according to claim 1, wherein, the controller is configured as an internal controller integrated in the body portion; and/or the controller is configured as an external controller separated from the body portion.

10. The air purification device according to claim 9, wherein, the external controller is mounted in the space of air to be conditioned and is integrated with temperature/humidity control module.

11. The air purification device according to claim 1, wherein, the body portion of the air purification device is arranged at an air outlet or an air inlet of the space of air to be conditioned.

* * * * *